United States Patent [19]

Schneider et al.

[11] Patent Number: 4,869,725

[45] Date of Patent: Sep. 26, 1989

[54] ENTERAL FEEDING BAG

[75] Inventors: James G. Schneider, St. Louis; James A. Geil, St. John, both of Mo.

[73] Assignee: Sherwood Medical Company, St. Louis, Mo.

[21] Appl. No.: 918,782

[22] Filed: Oct. 14, 1986

[51] Int. Cl.[4] .................... A61B 19/00

[52] U.S. Cl. .................... 604/408; 383/22; 383/33; 383/63; 604/262; 604/279

[58] Field of Search .................... 604/77, 262, 277, 279, 604/335, 408, 415; 128/DIG. 24; 383/9, 17, 22, 33, 35, 63, 65, 97; 150/900

[56] References Cited

U.S. PATENT DOCUMENTS

| | | | |
|---|---|---|---|
| 1,982,845 | 12/1934 | Wagman | 383/97 |
| 3,163,164 | 12/1964 | Waldman, Jr. | 604/262 |
| 3,251,390 | 5/1966 | Evans . | |
| 3,331,421 | 7/1967 | Lambert | 383/9 |
| 3,346,883 | 10/1967 | Ersek | 383/33 |
| 3,395,788 | 8/1968 | Gill | 383/35 |
| 3,437,117 | 4/1969 | Vitello et al. | 383/22 |
| 3,473,532 | 10/1969 | Eisenberg . | |
| 3,724,461 | 4/1973 | Eisenberg . | |
| 3,734,154 | 5/1973 | Polk | 128/DIG. 24 |
| 3,825,005 | 7/1974 | Fenton | 604/335 |
| 4,161,179 | 7/1979 | Abramson . | |
| 4,230,115 | 10/1980 | Walz, Jr. et al. | 128/DIG. 24 |
| 4,278,198 | 7/1981 | Norton et al. . | |
| 4,363,345 | 12/1982 | Scheibner | 383/35 |
| 4,525,156 | 6/1985 | Benusa et al. | 604/28 |
| 4,619,021 | 10/1986 | Johnson . | |
| 4,620,320 | 10/1986 | Sullivan . | |

*Primary Examiner*—C. Fred Rosenbaum
*Assistant Examiner*—Mario Costantino
*Attorney, Agent, or Firm*—Stanley N. Garber; Andrew J. Beck; William R. O'Meara

[57] ABSTRACT

An enteral feeding bag apparatus comprising an open-mouth flexible bag which is maintained in open condition by means of an opening maintaining plate member, is sealable by means of a liquid tight zipper lock closure means and is suspendable by a reinforced hanger portion for filling and/or administration of an enteric feeding composition.

9 Claims, 2 Drawing Sheets

ENTERAL FEEDING BAG

SUMMARY OF THE INVENTION

This invention relates to apparatus for administering fluids, such as naso-gastric or enteric feeding compositions to patients in hospitals, nursing homes and the like. More particularly, this invention relates to an easily closed and sealed large-mouth flexible bag for holding and storing such enteric feeding compositions before and during such feeding procedures, whereby the bag is easily maintained in mouth-open condition for ease of filling, and may very easily be sealed for flat storage, i.e. under refrigeration, and can be hung or disposed flat for administration of the contents.

The enteral feeding bag of this invention is preferably formed of an imperforate flexible plastic material such as polyvinyl chloride, polyethylene, polypropylene or the like of a transparent or translucent quality. It is readily attached to a hanger bracket or hook support. A delivery tube may be attached or sealed into the bottom of the bag and liquid level indicia may be provided to indicate quantities of liquids therein.

It is a primary object of this invention to provide an improved bag construction for the above-stated purposes, which features improved facility for the user when handling and filling the bag as from a pitcher, beaker, faucet, tube or the like.

Another object is to provide an improved bag which is easily sealed after being filled and easily reopened for refilling, as required.

Still another object is to provide an improved bag which can be filled while suspended from a hanger bracket or hook without requiring one or both hands to maintain the bag mouth in open condition.

Other objects, features and advantages of this invention will be apparent from the following description and the accompanying drawings, wherein:

DESCRIPTION OF THE DRAWINGS

FIG. 4 is a partial front prospective view illustrating how the bag may be suspended from a hook, hanger bracket or the like;

DETAILED DESCRIPTION OF PREFERRED EMBODIMENT

Figure 1:
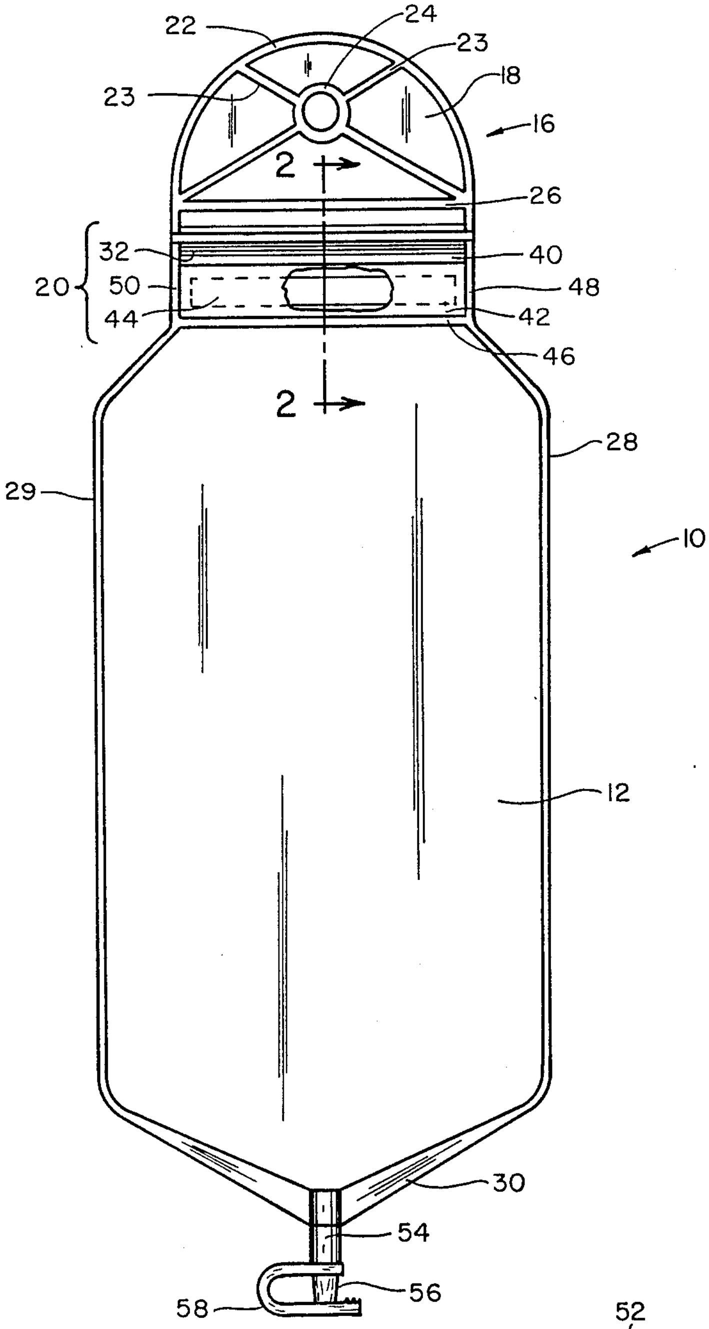
FIG. 1 is a front elevation view of the bag of the invention in normal unfilled condition.

As shown in FIG. 1 of the drawings, the enteral feeding bag of the present invention, indicated generally at 10, may be constructed of front and rear panels 12 and 14 of a flexible plastic film such as polyvinyl chloride, polyethylene, polypropylene or the like film which has been secured at the edges thereof by heat sealing, cementing or the like along seal lines 28, 29 and 30. The rear panel 14 of the feeding bag of the present invention is extended upward from the neck portion 20 containing the top opening of the bag 10, to form a hanger portion 16 which is strengthened by the use of a short reinforcing panel 18, and wherein the two panels 14 and 18 are sealed together at seal lines 22, 23 and 26. An aperture for accepting a hook or hanger bracket is defined by seal line 24, as shown in FIG. 1. A drain tube 54 is cemented or heat sealed into the bottom of the bag at seal line 30. The drain tube 54 can be supplied with a spike port 56 cemented into such drain tube 54 and a spike closure (not shown) carried by a flexible band 58, as shown in FIG. 1, if desired. Alternatively, drain tube 54 can be supplied with a tube of an administration set (not shown) adapted for controlling the drip flow from the feeding bag 10 and connection to an administration tube maintained in the patient's nose and esophagus for administering repeated enteric feedings.

Figure 2:
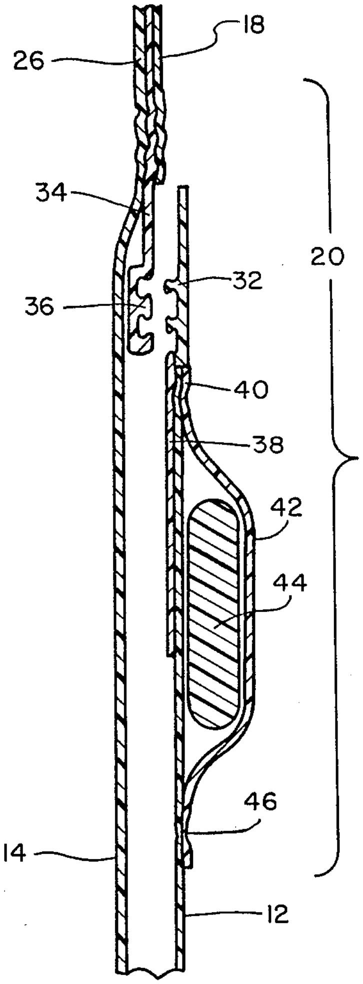
FIG. 2 is an enlarged partial side view in section taken along line 2—2 of FIG. 1.

Positive closure and sealing means for the feeding bag 10 of the present invention is provided by zipper lock means shown at 32 of FIG. 1 and in more detail at 32 and 36 of FIG. 2. The male segments 32 of the zipper lock closure are sealed to the front panel 12 of bag 10 at seal line 40 with an extension film 38 depending from seal line 40, while an extension film of the female segments 36 is sealed to the rear panel 14 and reinforcing panel 18 at seal line 26. The zipper lock closures 32 and 36 function in well-known manner to achieve an effective liquid sealed closure of the feeding bag 10, which can be quickly and easily opened for refilling and easily reclosed and resealed. The zipper lock closure can be any of such extruded plastic complementary mating convex protuberances and concave grooves which are commercially available, such as Ziploc ® closures from Dow Chemical Company or Flex-Tite ® closures from Minigrip, Incorporated. The zipper lock closures are sealably attached adjacent the top opening of the bag 10 in the neck portion 20 of bag 10, as shown. It will be apparent that, if desired, the male segments 32 may be attached to the rear panel 14 and the female segments 36 attached to the front panel 12 and they will function to effect a sealed closure in the same manner. A multiple number of mating curved surfaces has been found desirable to achieve a positive liquid sealed closure; thus sets of three convex male protuberances 32 and three concaved female grooves 36 are preferred over those zipper lock closures having only sets of two male and female members.

Figure 3:
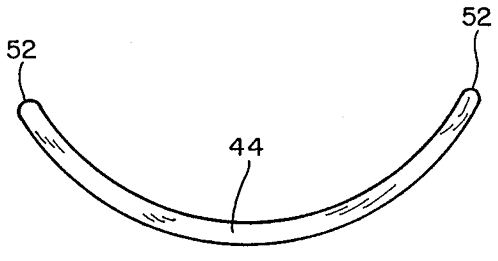
FIG. 3 is a top plan view of the rigid arcuate plate member of the preferred embodiment of the present invention.
Figure 4:
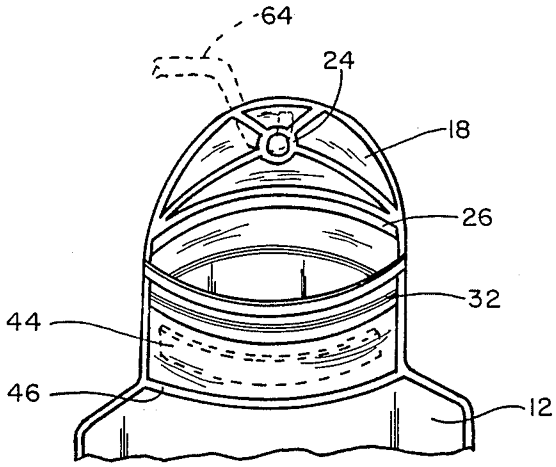

Adjacent to the zipper lock closure and also in the neck portion 20 of the bag 10 there is provided an opening maintaining member in the form of a plate member 44 enclosed within a sealed pouch formed from front panel 12 and pouch outer panel 42 sealed at seal lines 40, 46, 48 and 50 to form said sealed pouch. In a preferred embodiment of the present invention the plate member 44 is a substantially rigid arcuate plate with rounded ends 52, as shown in plan view in FIG. 3. Plate member 44 can be made of any substantially rigid molded plastic material such as a polycarbonate, i.e. Lexan polycarbonate of General Electric, nylon or polyoxymethylene, i.e. Delrin of duPont Company. The rigid arcuate form of plate member 44, in which the arch projects forward from the front panel 12 of bag 10 serves to maintain the opening of bag 10 in open condition when held upright or suspended by the hanger portion 16 from a hook 64 or hanger bracket, as shown in FIG. 4. When initially selected for use and when the neck portion 20 is closed by the closure means both the front and rear panels 12 and 14 which are the same width are arcuately curved from the front of the bag 10 because of the arcuate plate member 44. When pulled open by the user, the rear panel passes through the straight line width of said neck portion 20 and assumes an arcuate curve from the rear of said bag 10 and this curve is maintained by the added stiffness supplied by the rear attached zipper lock segment 36. Thus, the mouth of bag 10 is maintained in fully open condition without external biasing forces being applied to neck portion 20. The maintenance of the bag 10 in fully open condition enables the user of the feeding bag of the present invention to fill same from a pitcher, beaker, faucet, tube or the like without requiring either of the user's hands to maintain the bag opening in open position for filling. Thus, the user's hands are left free to prepare, handle and pour the enteric feeding solutions without need for attention to the open condition of the opening of the feeding bag of the present invention.

Figure 5:
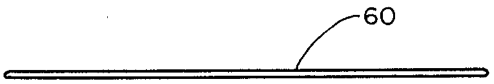
FIG. 5 is a top plan view corresponding to FIG. 3 but showing the flat, relatively stiff but flexible plate of a different embodiment of the present invention.

In another embodiment of the feeding bag of the present invention the opening maintaining member can take the form of a flat semi-rigid, but still flexible, plate member 60 as illustrated in plan view in FIG. 5. This form of the plate member 60 can conveniently be molded or cut from a relatively thick sheet of a semi-rigid plastic material such as polyethylene, polypropylene, polyvinyl chloride or the like. In the latter embodiment the opening of the feeding bag 10, once opened by the user, will easily be maintained in fully open condition by slight pressure at the sides of the opening. Such pressure can be exerted by the user's fingers of one hand or, alternatively, by a spring clip, rubber band, or like source of biasing pressure. When such an alternative source of biasing pressure is used, both the user's hands will remain free for handling and pouring the enteric feeding solutions to be administered. The maintenance of the feeding bag of the present invention in open condition contributes substantially to the ease of a pre-filling operation.

Upon closure of the opening of the bag of the present invention by tightly engaging the zipper lock segments 32 and a liquid tight seal is achieved enabling the user to dispose the filled bags horizontally for efficient storage in a refrigerator or on a table or shelf without danger of any leakage occuring. When required for administration, the filled feeding bag of the present invention can be removed from storage, hung on a hook or hanger bracket, an administration set attached, if not already so attached, and the set assembled to an administration tube for the patient, with the convenience of pre-prepared feedings. Thus, it is seen that the enteral feeding bag of the present invention affords substantial improved convenience and time-saving during the pre-filling operation as compared to such enteric feeding bags as are presently available on the medical market.

Although the foregoing description and the drawings describe and illustrate two embodiments of the enteral feeding bag of the present invention that fulfill the objects and advantages sought therefore, variations and modifications thereof are contemplated as may be apparent to those skilled in the art and as may be accomplished within the scope of the claims which follow.

What is claimed is:

1. An enteral feeding device comprising a pair of flexible plastic panels peripherally connected together in facing relation and shaped to provide a bag having a neck with a width less than that of other portions of said bag, said bag having a large opening at the upper end of said neck, closure means including plastic zipper lock closure means for sealingly closing said opening, said closure means including complementary male and female closure strips respectively connected to the inner sides of said panels in facing relation adjacent to the upper end of said neck and extending laterally between the opposed sides of said neck, said male closure strip having protuberance means and said female closure means having groove means for receiving said protuberance means when manually urged together for closing the opening, a hanger member connected to one of said panels and extending above the upper end of the other of said panels for hanging the bag from a support member, a plate member connected to one of said panels and extending between said opposed sides of said necks below said closure strips for assisting in holding the end of said neck open during the filling of the bag with an external composition, and aperture means at the bottom of said bag for feeding the enteric composition from said bag to a patient when the device is in use.

2. The enteral feeding bag of claim 1 which includes a sealed in closable feeding tube connection at its lower end.

3. The enteral feeding bag of claim 1 wherein said plate member is substantially thicker than said front and rear panels.

4. The enteral feeding bag of claim 1 wherein said plate member comprises a, relatively stiff, flexible flat plate which is stiffer than the panels.

5. The enteral feeding bag of claim 1 wherein said plate member comprises a substantially rigid arcuate plate.

6. The enteral feeding bag of claim 1 wherein one of said panels includes a double-walled pouch, said plate member is disposed in said pouch.

7. The enteral feeding bag of claim 1 wherein said panels are comprised of a flexible plastic sheet material selected from polyvinyl chloride film, polyethylene film or polypropylene film.

8. The enteral feeding bag of claim 1 wherein said plate member is comprised of a plastic material stiffer than that of said panels and selected from polyethylene, polypropylene or polyvinyl chloride.

9. The enteral feeding bag of claim 1 wherein said plate member is comprised of a substantially rigid plastic material selected from polycarbonate, polyoxymethylene or nylon.

* * * * *